US005643220A

United States Patent [19]
Cosme

[11] Patent Number: 5,643,220
[45] Date of Patent: Jul. 1, 1997

[54] NEEDLE ASSEMBLY

[76] Inventor: Edgar Z. Cosme, 1626 Peacock La., Fullerton, Calif. 92633

[21] Appl. No.: 698,441

[22] Filed: Aug. 19, 1996

[51] Int. Cl.$^6$ .................................... A61M 5/32
[52] U.S. Cl. .................................... 604/192; 604/263
[58] Field of Search .................. 604/272, 192, 604/198, 195, 187, 263

[56]  References Cited

U.S. PATENT DOCUMENTS

| 1,921,034 | 8/1933 | La Marche | 604/198 |
| 5,108,378 | 4/1992 | Firth et al. | 604/192 |

Primary Examiner—John D. Yasko
Attorney, Agent, or Firm—Maria Erlinda C. Sarno

[57]  ABSTRACT

A needle assembly with a needle holder, a needle sleeve movable over the needle holder, and an interlocking member. The needle sleeve encloses a needle holder and is manually extendable and retractable in a telescopic manner to enclose or expose respectively the distal sharp portion of a needle without the aid of a spring or spring-like device. In this assembly, the needle attached to a connector is embedded into the needle holder to prevent movement of the needle during use. Temporary locking and release means are provided which are simple and inexpensive in design.

14 Claims, 2 Drawing Sheets

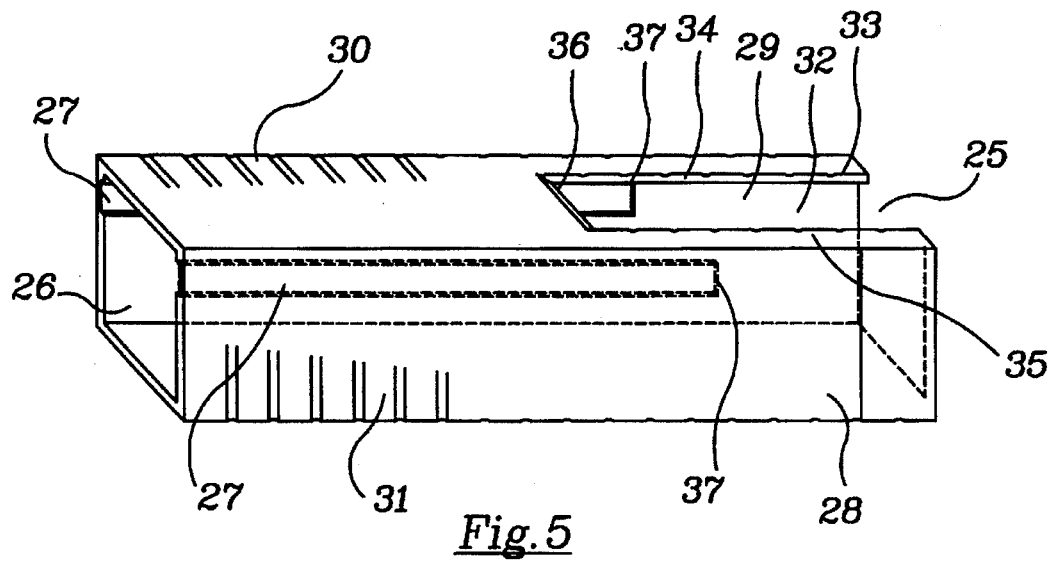
Fig. 5
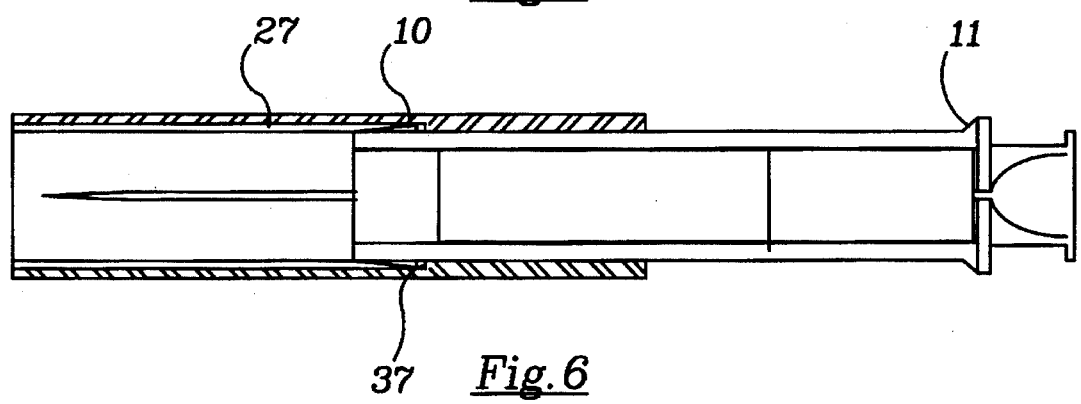
Fig. 6
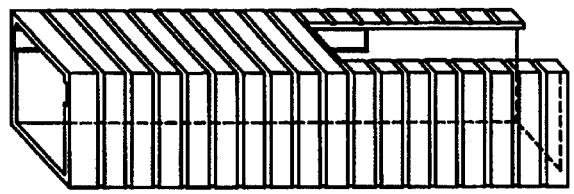
Fig. 7
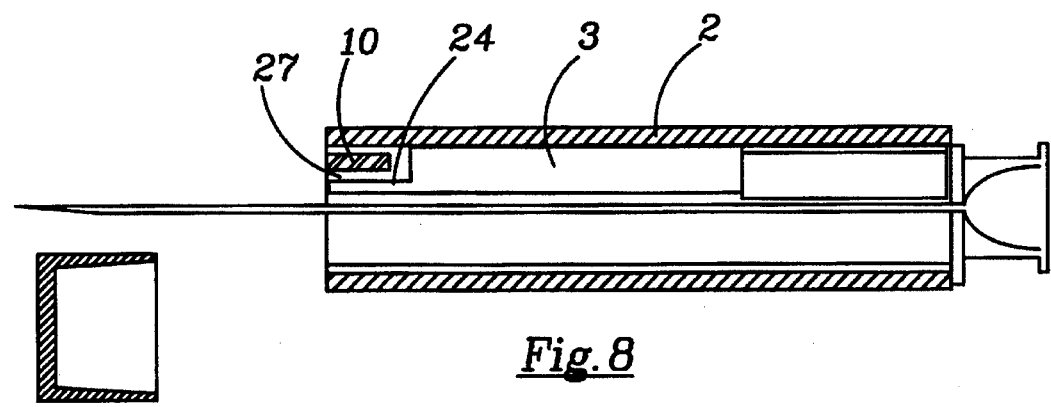
Fig. 8
Fig. 9

NEEDLE ASSEMBLY

BACKGROUND

The present invention relates to a needle assembly with a sliding needle sleeve to shield the sharp distal end of a needle. The needle assembly can be mounted on the forward end of a syringe body or other fluid delivery systems or reservoirs. A syringe utilizing this needle assembly offers protection to the user from unintended, accidental puncture.

It is well known that used syringe needles may cause serious illness or untimely death if a person gets accidentally scratched by a needle previously used on an infected individual. Paramedic and health care personnel in Emergency Room or in an emergency situation are particularly susceptible to receiving a scratch from a contaminated needle dislodged by the thrashing of an accident victim. Further, there has been a growing awareness of the danger of contracting AIDS or hepatitis from improperly discarded hypodermic needles.

The needle covers currently used in the medical field employ a conventional needle that is completely shielded by a removable plastic cover. The plastic cover is manually removed before an injection and manually recapped after use. For example, to recap after an injection, the user has to retrieve the needle from the patient and cover the needle with the plastic cover. Accidental puncture can occur while the user retrieves the needle from a patient and covers the needle. Accidental removal of the plastic cover is also possible when a covered needle is discarded which can prick or scratch a user or bystander.

There has been a number of attempts to design a needle cover with varying degrees of success. Most of these devices known in the art basically consist of two cylindrical components, with one sliding over or inside the other in a telescopic manner aided by a spring mechanism for automatic shielding and exposure of the needle. These needle covers differ in their locking mechanism. These covers are either hard to assemble due to the complexity of the mechanism or are expensive to manufacture.

It is therefore a prime object of the present invention to provide a needle assembly which protects the sharp tip of the needle from exposure prior to and during the mounting of the needle into the syringe body, between injections and after the needle has been discarded.

It is another object of the present invention to provide a needle assembly that is simple in design, providing ease of manufacture.

It is a further object of the invention to provide an inexpensive needle assembly that can be offered as a disposable product.

SUMMARY OF THE INVENTION

The present invention resides in a needle assembly that do not utilize a compressible spring device for covering or exposing the sharp distal tip of a needle by a sleeve. This needle assembly includes a needle holder, a needle sleeve and an interlocking member.

The needle holder is shaped like an open trough with a side extension or a scoop. It has an open lateral distal end and a closed walled proximal end, a walled first and second longitudinal sides, a solid base and a hollow top surface. Embedded on the upper portion of the solid base close to the hollow top surface is a metallic needle permanently attached to a connector which extends beyond the closed walled proximal end of the needle holder. The distal end of the needle protrudes. The needle assembly is commonly mounted to a hypodermic syringe but other fluid delivery devices may also be used with this assembly. A protrusion extends radially outward from the outer surface of the longitudinal walls at the distal end of the needle holder. The protrusion functions both as a stopping device between the needle holder and the needle sleeve. A needle sleeve, over and around the needle holder, slides rearward or forward, along the direction of the needle to shield or expose the needle. An interlocking member inserted into the needle holder locks or release the telescopic motion of the needle sleeve relative to the needle holder. Telescopic motion means the needle sleeve can slide rearward or forward over the needle holder from a position wherein the needle sleeve completely envelopes the needle holder to a position where the needle sleeve extends outward away from the needle holder.

BRIEF DESCRIPTION OF THE DRAWINGS

FIG. 5 is a perspective view of the needle sleeve.

FIG. 6 is a top view of the needle assembly with the needle shielded by the needle sleeve.

FIG. 7 is a perspective view of the needle sleeve with a fully gridded outer surface.

FIG. 8 is a side view of the needle assembly with the needle exposed.

FIG. 9 is an exploded side view of the capping component.

DETAILED DESCRIPTION OF THE INVENTION

Figure 1:
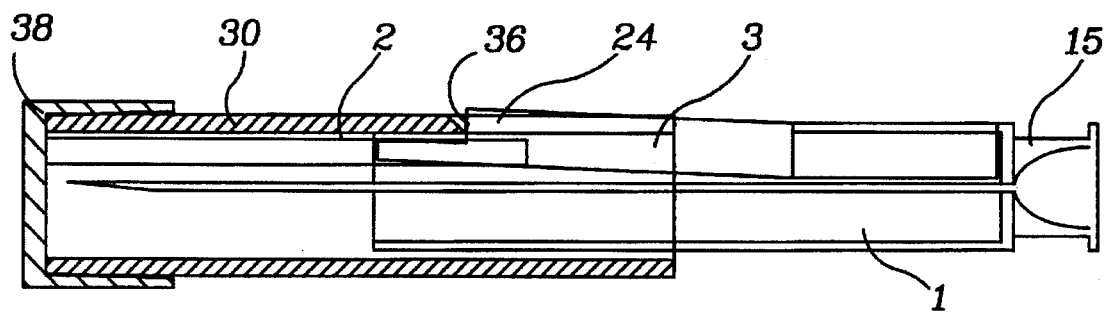
FIG. 1 is a side view of the needle assembly showing the needle covered by the needle sleeve and a cap.

The present invention resides in a needle assembly that do not utilize a compressible spring device for moving or locking a sleeve that covers the sharp distal tip of the needle. This needle assembly includes a needle holder 1, a needle sleeve 2 and an interlocking member 3 as shown in FIG. 1. In this invention, the distal end is the point away from the operator while the proximal end is the point close to the operator during the use of this device. The shape of the needle assembly is preferably rectangular for ease of handling.

Figure 2:
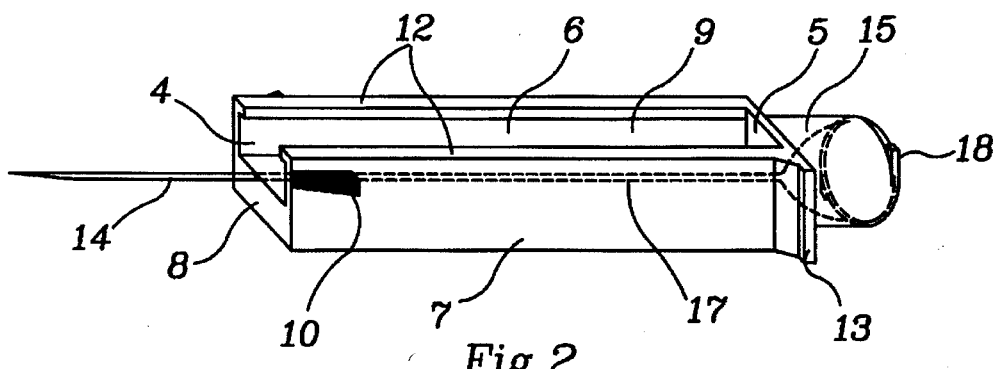
FIG. 2 is a perspective view of the needle holder with a connector having a luer lock tip.

The needle holder 1 is shaped like an open trough with a horizontal extension or a scoop as shown in FIG. 2. It has an open lateral distal end 4 and a closed walled proximal end 5, a walled first 6 and second 7 longitudinal sides, a solid base 8, a hollow top surface 9 and a protrusion 10. The needle holder may be made of glass, metal or plastic but is preferably made of plastic polymeric material such as polyvinyl chloride, polyethylene, polypropylene, nylon, polycarbon, polysulfone, and the like. The protrusion 10 at the distal end of the needle holder extends radially outward from the outer surface of the longitudinal walls along the longitudinal sides 6 and 7 at the distal end of the needle holder. The protrusion 10 is preferably slanted, with the thicker end towards the proximal end and is also preferably made of the same polymeric material as the body of the needle holder. The solid base 8 is approximately half of the depth of the needle holder as shown in FIG. 2. The walls along the longitudinal sides 6 and 7 has an overhang 12 bordering the entire length of the longitudinal walls and extending internally, that is, inwardly towards the interior of the needle body. The wall that borders the proximal lateral end 5, extends slightly pass the longitudinal walls 6 and 7 to cause a protruding fence 13 which can be either on one side or on both sides of the proximal lateral end 5. The distal lateral end 4 is left open. Embedded on the upper portion of the solid base 8 close to the hollow top surface 9 is a metallic needle 14 with the distal end protruding from the needle holder 1 as shown in FIG. 2. The needle has a hollow interior, lumen 17 and could vary in sizes and gauge. The proximal end of the needle 14 is permanently mounted to one end of a connector 15 which is preferably made of the same polymeric material as the needle holder. A connector with a luer lock tip 18 at the other end not connected to the needle is preferred. The walls of the connector may be in line with the longitudinal sides of the needle holder or may be recessed as shown in FIG. 1. The connector 15 has a hollow conical interior, a cone shaped cavity, that tapers and converge with the proximal base of the hollow metallic needle 14 so as to communicate with the lumen 17 of the needle, through which materials, preferably liquids or suspensions, may be introduced. The needle assembly is commonly mounted into a hypodermic syringe or other fluid delivery source or reservoirs used and known in the medical field. The needle assembly is preferably mounted on a syringe body with a luer lock adapter. The protrusion 10 that extends radially outward from the outer surface of the walls covering longitudinal sides 6 and 7 at its distal end functions both as a locking device and an engagement device with the needle sleeve 2.

Figure 3:
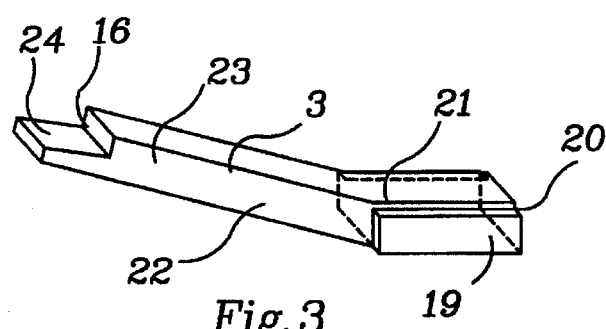
FIG. 3 is a perspective view of the interlock member.
Figure 4:
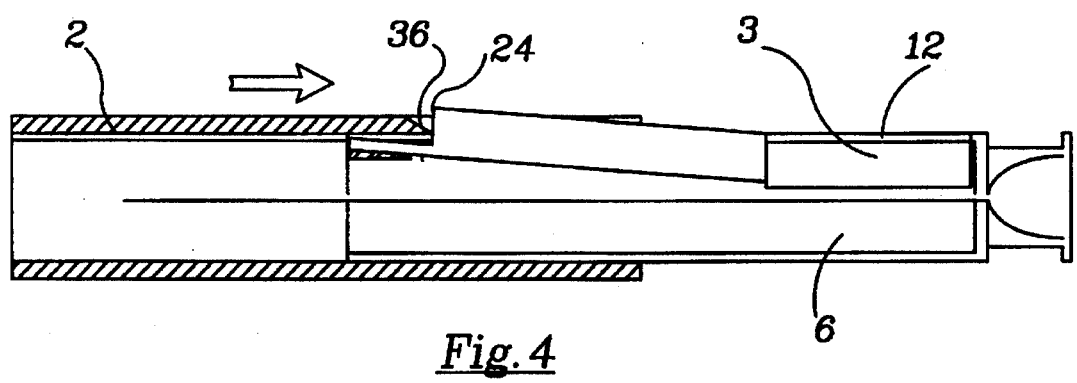
FIG. 4 is a side view of the needle assembly with the interlocking member inside the hollow top surface of the needle holder and abutting upon the needle sleeve.

An interlocking member 3 as shown in FIG. 3 slips or snaps into the hollow top surface of the needle holder and is held inside the hollow top surface 9 by the overhang 12 along the longitudinal walls 6 and 7 as shown in FIG. 4. The interlocking member is solid. It can be made of metal or hard rubber but is preferably made of the same preferred polymeric material used for the needle holder 1 but is of a kind that is non-brittle, durable and resilient with memory. With memory means the material will return to its original configuration when the restraining means which keeps the material stationary at a strained position, is released. The proximal portion 19 of the interlocking member is planar with a recess 20 along its longitudinal edges 21 as shown in FIG. 3. The recess 20 abuts and fits underneath the overhang 12 of the needle holder 1. The outer surfaces of the recess 20 and the overhang 12 are shaped to match each other and are of the same dimensions to allow a good fit. They are preferably planar. The distal portion of the interlocking member 3 extends upwardly at an angle, hereinafter referred to as angular end 22, from its planar proximal end 19. The angular end 22 has a width narrower than the planar end 19. The angular end has no recess along its longitudinal edges 23. The angular end is also of such width that its longitudinal edges 23 just freely rub on the longitudinal inside tip of the overhang 12, allowing unimpeded up and down motion of the angular end 22. At the distal portion of the angular end 22 is a second stepped recess which look like a fore and middle finger projection, hence will be referred to as finger hook 24. The finger hook has a notch 16.

The needle sleeve 2 is shaped to conform with the outer contour and surface of the needle holder 1. It is preferably shaped like a hollow rectangular box, as shown in FIG. 5, with an open proximal 25 and distal 26 lateral ends to allow the needle sleeve 2 to slide over the needle holder 1 in a telescopic manner relative to the needle holder. The closed sides of the needle sleeve are the longitudinal side walls 28 and 29 and the top and bottom surfaces 30 and 31. The top surface 30 has a cutout area 32, preferably rectangular in shape as shown in FIG. 5. The cutout area has three sides, two horizontal sides 34 and 35 and a frontal side 36. All three sides may be blunt ended but it is preferable for the frontal side 36 to have a slant edge as shown in FIG. 4. The cut out area leaves a horizontal overhang 33 which rests over the overhang 12 of the needle holder 1, The overhang 12 functions like a track over which the sleeve traverses to and from. At a calculated or measured distance, starting approximately a third of the full length of the needle sleeve 2 from the proximal end 25, are grooves 27 along the inner surface of the longitudinal walls. These grooves engage with the protrusion 10 and function as a track (shown in broken line) through which the protrusion 10 can traverse to and from horizontally as shown in FIG. 6. The outer surface of the longitudinal walls 28 and 29 of the needle sleeve may be smooth or gridded. However, it is preferable to grid all the outer sides of the walls to provide a better grip for the user as shown in FIG. 7. The needle sleeve can also be made of metal or glass but is preferably made of the same polymeric material as those used for the needle holder and interlocking member.

When the sliding needle sleeve 2 is slid over the top surface of the needle holder from a position covering the needle holder as shown in FIG. 8, to a direction towards the tip of the needle 14, the leafspring action of the angular end 22 allows the finger hook to rest on the inside wall of the top surface 30 of the sliding needle sleeve and the notch 16 to rest on its frontal side 36 as shown in FIG. 1. At this position, the entire needle is shielded and the sleeve is temporarily locked. Leafspring effect is the counter effect produced when the upward distal end of the interlock member is pressed downward while the planar proximal end 19 is kept stationary in one position. The needle assembly with the needle sleeve 2 in this forward position, shielding the needle 14, is temporarily locked in this position by the finger hook 24 abutting on the frontal side 36 of the cutout area afforded by its leafspring effect. The finger hook 24 protrudes over the top surface 30 thereby preventing the needle sleeve 2 from moving away from the direction of the needle, as shown in FIG. 1. On the other hand, the forward motion of the needle sleeve 2 towards the direction of the needle is checked when the protrusion 10 abuts at the end 37 of the groove 27 as shown in FIG. 6. The grooves 27 prevent the needle sleeve 2 from disengaging with the protrusion 10 of the needle holder.

The procedure for exposing the distal tip of the needle 14 from a position where the needle sleeve 2 shields the entire needle body is accomplished by pressing on the top surface of the finger hook 24 downward, towards the hollow top surface 9 of the needle holder, to release its engagement from the frontal side 36. Once the finger hook 24 no longer abuts on the frontal side 36, the needle sleeve can be manually moved rearward or slid rearward in a direction away from the needle, thereby exposing its distal end as shown in FIG. 8. At this position, the needle is free for usage for any purpose such as injection, infusion, pricking and the like. The needle sleeve 2 is kept from moving forward or rearward during its use by the slightly flaired edge 11 at the outside junction between the longitudinal walls 6 and 7 and the fence 13. Further, since the inside surface dimensions of the needle sleeve is barely larger than the outer surface dimensions of the needle holder, only enough to allow it to slide over the needle holder, there is also provided a frictional resistance to unassisted motion. The protruding fence 13 on one or both sides of the proximal end 5 of the needle holder also stops any further rearward motion of the needle sleeve 2. After use, the needle sleeve 2 is merely pushed forward to a position wherein the finger hook 24 reengages automatically with the frontal side 36 because of the angular design and leafspring effect of the distal portion of the interlock member. This process allows one to manually slide with ease, the needle sleeve 2, forward and rearward in relation to the needle holder 1, to cover and uncover the sharp distal end of the needle 14 without the use of a spring device and complex mechanisms.

For packaging, shipping or when discarding the needle assembly after use, it is preferable to incorporate a capping component 38 for covering the distal and the proximal end of the needle assembly to further prevent accidental puncture or scratching with the tip of the needle. The cap can be made of metal or glass but is preferably made the same polymeric material as those used for the other components of the needle assembly. As shown in FIG. 1, it is sufficient to have only one cap covering the open distal end of the needle assembly if the entire assembly, for example, will be packaged inside a pouch or container. If only one cap is used, the cap 38 extends preferably from the distal tip of the needle sleeve to a position in front of the finger hook 24 which protrudes over the needle sleeve 2 when the needle assembly is stored or discarded as shown in FIG. 1. The inner wall of the cap 38 is thicker at its distal end than at its proximal end to cause the cap to receive and fit snugly into the needle assembly thereby preventing the cap 38 from unassisted slippage as shown in FIG. 8.

Due to the simplicity in design of the needle assembly and the availability of needles and suitable plastic materials at rather reasonable prices, this device can be made available as a disposable product for one time or limited time usage.

While the embodiment of the present invention has been described, it should be understood that various changes, adaptations, and modifications may be made therein without departing from the spirit of the invention and the scope of the appended claims.

What is claimed is:

1. A needle assembly for use with a fluid delivery device, comprising:
   a needle holder having a closed walled proximal end, an open distal end, a walled first and second longitudinal side, a solid base, a hollow top surface, a hollow needle embedded to the solid base, and a two ended hollow connector mounted to the needle at one end;
   a sliding needle sleeve for surrounding the needle holder, the sleeve slidably movable relative to the needle holder in the direction of the length of the needle from a first position in which the needle projects outside of the needle sleeve to a second position in which the needle is within the needle sleeve;
   means for engaging the needle holder with the needle sleeve;
   means for interlocking the needle sleeve with the needle holder; and,
   means for stopping the rearward and forward motion of the needle sleeve relative to the needle holder.

2. The needle assembly of claim 1 wherein the needle assembly is made of plastic polymeric material.

3. The needle assembly of claim 2 wherein the polymeric material is selected from the group consisting of polyvinyl chloride, polyethylene, polypropylene, nylon, polycarbon and polysulfone.

4. The needle assembly of claim 1 wherein the needle assembly is rectangular in shape.

5. The needle assembly of claim 1 wherein the first and second longitudinal walls of the needle holder have overhangs bordering the entire length of the walls and directed inwards for receiving an interlocking means.

6. The needle assembly of claim 1 wherein the hollow needle has a lumen in direct communication with the hollow connector.

7. The needle assembly of claim 1 wherein the hollow connector mounted to the hollow needle has a conical interior cavity tapering into the lumen of the needle.

8. The needle assembly of claim 1 wherein the other end of the hollow connector not mounted on the needle has a luer lock tip.

9. The needle assembly of claim 1 wherein the needle sleeve has a gridded area on the outer surface.

10. The needle assembly of claim 1 further comprising of a cap means for closing an end of the needle assembly.

11. The needle assembly of claim 1 wherein the needle assembly is disposable.

12. A needle assembly for use with a fluid delivery source, comprising:
   a needle holder having a walled first and second longitudinal side, an overhang directed internally bordering along the entire length of the first and second longitudinal walls, a protrusion on the distal outer surface of the first and second longitudinal walls, an open distal end, a closed walled proximal end, the closed proximal end wall extending slightly beyond the first and second longitudinal walls, a solid base, a hollow top surface, a hollow needle embedded on the solid base and a two ended hollow connector mounted to the hollow needle on one end;
   an interlocking member having a planar proximal end and an angular distal end, the distal end narrower than the proximal end, a step recess on the longitudinal sides of the planar proximal end abutting on the overhang along the first and second longitudinal walls of the needle holder when introduced therethrough, and a finger hook on the distal angular end for engagement and release;
   a needle sleeve for surrounding the needle holder, having an open proximal and distal end to receive the needle holder therethrough, closed walled longitudinal, bottom and top surfaces, a groove along the inner surface of the longitudinal wall for engaging with the protrusion on the outer surface of the needle holder thereby permitting traversal of the protrusion along the groove, a cut out area on the top surface for engaging with the finger hook of the interlocking member thereby temporarily locking the needle sleeve to a position shielding the distal tip of the hollow needle; and,
   means for controlling the position of the needle sleeve relative to the needle holder thereby shielding or exposing the hollow needle as desired.

13. The needle assembly of claim 10 further comprising a cap means for closing an end of the needle assembly.

14. The needle assembly of claim 10 wherein the needle assembly is disposable.

* * * * *